United States Patent [19]

Photis

[11] 4,180,674

[45] Dec. 25, 1979

[54] PROCESS FOR PREPARING BUTYL-P-BENZOYLBENZOATES

[75] Inventor: James M. Photis, Ridgefield, Conn.

[73] Assignee: Stauffer Chemical Company, Westport, Conn.

[21] Appl. No.: 816,772

[22] Filed: Jul. 18, 1977

[51] Int. Cl.$^2$ .............................................. C07C 69/78
[52] U.S. Cl. ..................................................... 560/52
[58] Field of Search .......................................... 560/52

[56] References Cited

PUBLICATIONS

Le Fare et al., "J. Am. Chem. Soc.", vol. 72,(1950), pp. 2464 and 2465.

*Primary Examiner*—Joseph E. Evans
*Attorney, Agent, or Firm*—Ellen P. Trevors; William R. Robinson; William C. Gerstenzang

[57] ABSTRACT

Butyl-p-benzoylbenzoates are prepared by reacting a 4-(trichloromethyl) benzophenone with a butanol in the presence of an acid catalyst. These butyl-p-benzoylbenzoates are valuable photoinitiators for the polymerization of ethylenically unsaturated monomers.

5 Claims, No Drawings

PROCESS FOR PREPARING BUTYL-P-BENZOYLBENZOATES

BACKGROUND OF THE INVENTION

Substituted benzolybenzoates are known compounds which are usually produced by esterification of the corresponding carboxylic acid with the appropriate alcohol, or by the reaction of the benzoylbenzoic acid chloride with the alcohol. However, such processes are expensive and result in unacceptable yields, primarily because of the difficulty in producing the acid and acid chloride. Also, methods such as azeotropic distillation or addition of acid acceptors are necessary to drive these esterification reactions to completion.

Thus, Beilstein 10, 753 discloses the permangante oxidation of methyl benzophenone to provide benzoylbenzoic acid, a process requiring a large volume of water and resulting in the formation of waste manganese dioxide. Chromic acid oxidation of p-benzoltoluene to provide benzoylbenzoic acid is also disclosed, but this procedure requires a lengthly heating period and produces waste chromic sulfate, a suspected carcinogen. The acid chloride can be made by a Friedel-Crafts reaction of terephthaloyl chloride and benzene in the presence of aluminum trichloride, but the major product of this reaction is dibenzoylbenzene.

Now it has been found in accordance with this invention that butyl-p-benzoylbenzoates can be made by a process which avoids the preparation of the corresponding acid or acid chloride.

SUMMARY OF THE INVENTION

According to the process of this invention, butyl-p-benzoylbenzoates are made by reacting a 4-(trichloromethyl) benzophenone with a butanol in the presence of an acid catalyst.

DETAILED DESCRIPTION OF THE INVENTION

More in detail, the butyl-p-benzoylbenzoates prepared according to the process of this invention have the formula:

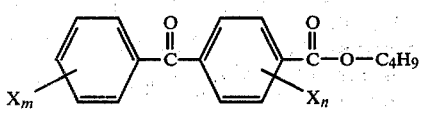

I where each X is an independently selected halogen and m and n are independently selected integers from 0 to 3. Illustrative compounds within the scope of formula I include n-butyl-p-benzoylbenzoate, iso-butyl-p-benzoylbenzoate, 4-carbo-n-butoxy-4'-fluorobenzophenone; 4-carbo-iso-butoxy-3-bromobenzophenone; 4-carbo-n-butoxy-3,4,4'-trichlorobenzophenone; etc.

The butyl-p-benzoylbenzoates having the formula I are prepared by the acid catalyzed reaction of the appropriate 4-(trichloromethyl) benzophenone with a butanol in accordance with the following equation where X, m and n are as previously described.

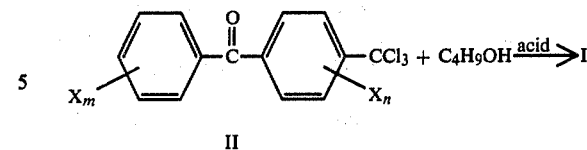

II

The 4-(trichloromethyl) benzophenones II are known compounds which are readily prepared by chlorinating the corresponding methyl benzophenones. Illustrative procedures for preparing the 4-(trichloromethyl) benzophenones II are described by Man and Hauser in J. Organic Chemistry 17, 397 (1952) and by Jensen et al. in J. American Chemical Society, 81, 3303 (1959).

While any of the 4-(trichloromethyl) benzophenone precursors represented by the formula II can be employed in the process of this invention, preferred embodiments utilize the unsubstituted compound, i.e., 4-(trichloromethyl) benzophenone.

The isomers of butanol such as n-butanol and iso-butanol readily react with the precursor II in the presence of an acid catalyst. Illustrative acid catalysts include strong acids such as hydrochloric acid, sulfuric acid, nitric acid, etc. The acid is generally employed in an amount between about 10 and about 20% by volume of the reaction mixture, based on the concentrated from of the particular acid.

In the process of this invention, it is preferred to employ 4 to 12 moles of alcohol per mole of precursor II. Although the process proceeds readily by refluxing under ambient pressure other conditions can be employed. Thus, the reaction can be carried out at temperatures between about 80° C. and 100° C. If desired, pressure equipment can be used although the reaction proceeds readily under ambient pressure.

After completion of the reaction, the desired butyl-p-benzoylbenzoate I is isolated from the reaction mixture by conventional techniques, such as filtration, evaporation, and the like.

The compounds I of this invention have a variety of useful applications. In particular, they have recently been found to be excellent photoinitiators for ethylenically unsaturated compounds. Thus, they can be employed in photopolymerizable molding and coating compositions which are applied to a substrate and exposed to light radiation having wave lengths of above 2000 Angstrom units and preferably from about 2000 Angstrom units to about 8000 Angstrom units.

The following example will serve to illustrate the practice of this invention.

EXAMPLE

To a mechanically stirred solution of 1000 grams (7.12 moles) of benzoyl chloride in 6000 grams of toluene was added 1000 grams (7.50 moles) of anhydrous aluminum chloride over a 20–30 minute period. The temperature of the reaction mixture rose to near the boiling point during the addition, and heating at reflux was maintained for three additional hours. After cooling, 1200 milliliters of water were added, slowly at first, followed by 1000 milliliters of concentrated hydrochloric acid. The organic layer was separated, washed twice with hot water and concentrated on a rotary evaporator. Vacuum distillation of the residual oil provided 1300 grams (93% yield) of white, semi-solid methyl benzophenone; (b.p. 180°–200° C., 10–15 mm Hg; m.p.

50° C.). The infrared spectrum revealed a carbonyl band at 1665 cm⁻.

The amount of 1300 grams (6.65 moles) of methyl benzophenone was then melted and heated to 170°–180° C. in a 2 liter two necked round bottom flask with magnetic stirring. Chlorine gas was introduced through a gas dispersion tube immersed below the liquid at a rate such that the characteristic greenish color of chlorine was not detectable in the exiting stream of hydrogen chloride. After 12 hours, the hot melt was poured into 8 liters of isopropyl alcohol. This mixture was chilled to −5 to 0° C. and the precipitated solid removed by suction filtration to provide 1600 grams (81% yield) of 4-(trichloromethyl) benzophenone, mp 109°–111° C. A carbonyl band at 1670 cm$^{-1}$ was noted in the infrared spectrum.

A mixture of 1600 grams (5.35 moles) of the 4-(trichloromethyl)benzophenone, 4000 milliliters of n-butanol and 2400 milliliters of 19% by weight aqueous hydrochloric acid was mechanically stirred at the reflux temperature (93° C. pot temperature) for three hours. Then three liters of water was added. The upper organic layer was separated and stirred with 4000 milliliters of 10% aqueous sodium carbonate solution. The organic layer was again separated and washed twice with hot water. Removal of volatile components under reduced pressure produced 1400 grams (93% yield) of semi-solid, offwhite n-butyl-p-benzoylbenzoate, m.p. 50°–60° C. Carbonyl bands in the infrared spectrum at 1670 and 1730 cm$^{-1}$ confirmed the structure of the product.

Varying concentrations of the n-butyl-p-benzoylbenzoate were added to samples of a standard test solution consisting of 42% by weight of trimethylolpropane triacrylate, 17% by weight of ethylhexyl acrylate and 41% by weight of ACTOMER X-80 ® Resin, an unsaturated long chain linseed oil alkyl resin available from Union Carbide Corporation.

Cure rates were determined in air using as a source of actinic light a PPG Model QC 1202 AN UV Processor manufactured by PPG Industries, Inc. The radiation source for this apparatus consists of two high intensity medium pressure quartz mercury lamps 12 inches in length and each operating at a linear power density of about 200 watts per inch or 2400 watts per lamp. The lamps are housed in an elliptical reflector above a variable speed conveyor belt and each lamp provides a 2-inch band of high flux actinic radiation on the conveyor. This 2-inch exposure area is bordered on both sides by an additional 2-inch area of medium flux energy for a total radiation area of 6 inches for each lamp. In the curing data presented below, cure rate of the polymerizable composition is presented in feet-per-minute-per lamp (ft./min./lamp). Thus, a conveyor belt speed of one foot/min. will, with a 12-inch exposure area for the two lamps, provide 60 seconds of exposure or a cure rate of 0.5 ft./min./lamp. Similarly, a belt speed of 10 ft./min./will provide 6 seconds of exposure or a rate of 5.0 ft./min./lamp while a speed of 20.0 ft./min will give 3 seconds exposure or a rate of 10 ft./min./lamp, etc. The cure data is presented below. Where ranges for cure rates are indicated, several samples were tested, with purer esters giving the faster rates.

| SAMPLE | CONCENTRATION (% Wt.) OF N-BUTYL-p-BENZOYLBENZOATE | CURE RATE (Ft./Min./Lamp) |
|---|---|---|
| 1 | 2 | 7.5–10 |
| 2 | 4 | 15–20 |
| 3 | 6 | 20– |
| 4 | 8 | 20–35 |
| 5 | 10 | 30– |

The amount of 4% by weight of the n-butyl-p-benzoyl benzoate was also added to resin samples comprising 60% by weight of EPOCYRL ® resin DRH-303, a diacrylate ester of Bisphenol A epoxy resin available from Shell Chemical Company, and 40% by weight of 1,6-hexanediol diacrylate available from Celanese Corporation. A cure rate ranging from 30 to 40 ft./min./lamp was obtained for several samples.

What is claimed is:

1. A one step process for preparing butyl-p-benzoylbenzoates comprising:

reacting a 4-(trichloromethyl) benzophenone having the formula:

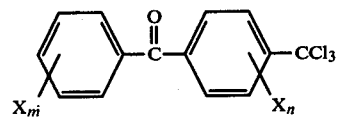

where each X is an independently selected halogen and m and n are independently selected integers from 0 to 3, with a butanol selected from the group consisting of n-butanol and iso-butanol in the presence of a catalytic amount of a strong mineral acid.

2. The process of claim 1 wherein the reaction is carried out at a temperature between about 80° C. and about 100° C.

3. The process of claim 2 wherein the reaction is carried out at the reflux temperature.

4. The process of claim 1 wherein n-butyl-p-benzoylbenzoate is prepared by reacting 4-(trichloromethyl) benzophenone with n-butanol.

5. The process of claim 4 wherein the acid catalyst is hydrochloric acid.

* * * * *

UNITED STATES PATENT AND TRADEMARK OFFICE
CERTIFICATE OF CORRECTION

PATENT NO. : 4,180,674
DATED : December 25, 1979
INVENTOR(S) : James M. Photis

It is certified that error appears in the above-identified patent and that said Letters Patent are hereby corrected as shown below:

Col. 1, line 7 - "benzolybenzoates" should be -- benzoylbenzoates --.

Col. 1, line 25 - "lengthly" should be -- lengthy --.

Col. 2, line 28 - "from" should be -- form --.

Col. 3, line 2 - "cm $^-$" should be -- cm$^{-1}$ --.

Signed and Sealed this

First Day of April 1980

[SEAL]

Attest:

SIDNEY A. DIAMOND

Attesting Officer

Commissioner of Patents and Trademarks

Disclaimer and Dedication

4,180,674.—*James M. Photis*, Ridgefield, Conn. PROCESS FOR PREPARING BUTYL-P-BENZOYL-BENZOATES. Patent dated Dec. 25, 1979. Disclaimer and Dedication filed May 27, 1980, by the assignee, *Stauffer Chemical Company*.

Hereby disclaims and dedicates to the Public the entire remaining term of said patent.

[*Official Gazette August 26, 1980.*]